(12) United States Patent
Carlton et al.

(10) Patent No.: US 7,008,599 B1
(45) Date of Patent: Mar. 7, 2006

(54) HIGH THROUGHPUT CRYSTAL FORM SCREENING WORKSTATION AND METHOD OF USE

(75) Inventors: David Leroy Carlton, Durham, NC (US); Om Parkash Dhingra, Durham, NC (US); David Harlan Igo, Durham, NC (US); Phillip William Waters, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/009,145

(22) PCT Filed: May 9, 2000

(86) PCT No.: PCT/US00/12610

§ 371 (c)(1),
(2), (4) Date: Nov. 8, 2001

(87) PCT Pub. No.: WO00/67872

PCT Pub. Date: Nov. 16, 2000

Related U.S. Application Data

(60) Provisional application No. 60/133,301, filed on May 10, 1999.

(51) Int. Cl.
*B01D 9/00* (2006.01)
(52) U.S. Cl. .................. 422/254; 422/245.1; 422/253; 422/255; 422/267; 422/282
(58) Field of Classification Search ............. 422/245.1, 422/253–255, 267, 282
See application file for complete search history.

(56) References Cited

U.S. PATENT DOCUMENTS

| | | | | |
|---|---|---|---|---|
| 3,670,889 A | * | 6/1972 | Brown et al. | 210/90 |
| 3,892,539 A | * | 7/1975 | Midler, Jr. | 23/301 |
| 3,930,951 A | * | 1/1976 | Messing | 435/176 |
| 4,848,139 A | * | 7/1989 | Blake-Coleman et al. | 73/61.75 |
| 4,919,804 A | * | 4/1990 | Dorsey et al. | 210/198.2 |
| 5,104,621 A | | 4/1992 | Pfost et al. | |
| 5,240,467 A | * | 8/1993 | Johnson | 23/296 |
| 5,814,277 A | | 9/1998 | Bell et al. | |

FOREIGN PATENT DOCUMENTS

| | | |
|---|---|---|
| EP | 0 553 539 | 8/1993 |
| EP | 0 565 844 | 10/1993 |
| GB | 2 249 492 | 5/1992 |
| WO | WO 9307311 A1 * | 4/1993 |

* cited by examiner

*Primary Examiner*—Yelena G. Gakh
(74) *Attorney, Agent, or Firm*—J. Michael Strickland

(57) ABSTRACT

A filtration assembly operable in connection with a crystal form screening workstation that provides for automated crystal form screening is disclosed. The assembly includes first and second valves, with each valve having an internal passage and first, second and third ports. A filter line is interposed between the first and second valves in fluid communication with the second port of the first valve and the second port of the second valve. A filter medium is in disposed in or at the end of the filter line and adapted to filter a drug-containing suspension flowing through the filter line. The filter medium is operable to filter fluids under both positive and negative pressure conditions.

18 Claims, 11 Drawing Sheets

HIGH THROUGHPUT CRYSTAL FORM SCREENING WORKSTATION AND METHOD OF USE

This application is filed pursuant to 35 U.S.C. §371 as a United States National Phase Application of International Application No. PCT/US00/12610 filed 9 May 2000, which claims priority from U.S. Application No. 60/133,301 filed 10 May 1999.

TECHNICAL FIELD

The present invention relates to a process and apparatus for preparing and analyzing liquid substances, and more particularly to a process and apparatus for automating the growth and screening of crystal forms.

BACKGROUND ART

In the field of drug research, chemists search for the optimal experiment conditions (e.g., reagents, temperatures) that will lead to the purest material. The route most often chosen involves purification of the drug substance via the generation of a crystalline form of that same drug substance. It is well known that a drug may have the potential to crystallize in a number of different forms. These forms differ in the spatial orientation of the drug molecule in the unit cell of a crystal lattice and possibly the inclusion and location of solvent molecules within the lattice structure. Significant research activity is employed to evaluate the way in which a drug substance crystallizes. Reason being, the crystal form of a drug can significantly influence i) how quickly it can dissolve, ii) how stable it will be, and iii) how easily it can be manufactured into a formulation. If a drug does not dissolve in the appropriate region of the body, then the body cannot properly absorb it and the likelihood of the drug reaching its target is compromised. If a drug is not stable, the shelf-life of the product may be reduced. If the drug cannot be easily manufactured into a formulation, the development costs may increase significantly.

The protocol for screening crystal forms may generally involve: (1) dissolving the drug in a solvent medium, (2) evaporating solvent, cooling the drug/solvent mixture, or adding an antisolvent to increase the degree of supersaturation of the drug in the solvent medium and (3) characterizing the resulting products using techniques such as polarized light microscopy, thermal analysis, Raman spectroscopy, and X-ray powder diffraction. Determining the amount of drug dissolved in the solvent medium provides a means of classifying the solvating power of the solvent. This information is useful in subsequent crystallizations. In order to produce the most suitable crystal form, hundreds or even thousands of individual experiments may have to be conducted. Unfortunately, most of the screening must be performed manually. Thus, the process remains quite time consuming and labor intensive.

Accordingly, those skilled in the art appreciate the need for increased automation of the process of screening for crystal forms in order to reduce the degree of human intervention required by the process and to improve the accuracy, efficiency, reliability and repeatability of the process. Also recognized is the need for a single apparatus that integrates preparation, growth and in situ analysis of crystal forms. The present invention, as described hereinafter in the context of preferred embodiments and processes, is provided to meet these needs.

DISCLOSURE OF THE INVENTION

In accordance with the present invention, there is provided as a first embodiment a filtration assembly for use in a fluid handling system. The filtration assembly is adapted to transfer fluid under the influence of either aspiration, positive displacement, peristalsis, or other fluid moving methods. The filtration assembly comprises first and second valves, with each valve having an internal passage and first, second and third ports. A filter line is interposed between the first and second valves in fluid communication with the second port of the first valve and the second port of the second valve. A filter medium is disposed in the filter line and adapted to filter a drug-containing suspension flowing through the filter line. The filter medium is operable to filter fluids under both positive and negative fluid pressure conditions. A bypass line is interposed between the first and second valves in fluid communication with the third port of the first valve and the third port of the second valve. An actuator switches the internal passage of the first valve between first and second positions. The first position provides a fluid path through the internal passage between the first port and the second port, and the second position provides a fluid path through the internal passage between the first port and the third port.

The filtration assembly is integrated into a liquid handling system to produce a crystal form screening workstation. Accordingly, a dilution assembly is provided that includes a valve or manifold communicating with a syringe, a solvent inlet line and a transfer line. The transfer line is connected to the first port of the first valve of the filtration assembly. A sampling needle is in fluid communication with the third valve and is mounted to a support member. The support member is movable in three-dimensional space in response to programmed instructions. The workstation also includes a sample containment assembly adapted to hold an array of fluid containers accessible by the sampling needle.

In another embodiment according to the present invention, a crystal form screening workstation comprises a plurality of racks removably mounted to a first rack holder, wherein each rack is adapted to hold a plurality of vessels. A sampling needle is movably mounted to a first automated arm assembly. The first automated arm assembly is adapted to effect programmable manipulations of the sampling needle along paths extending within the vessels and over the racks. A fluid movement controller is provided to withdraw fluid from and deliver fluid to the vessels of the racks through the sampling needle. A first valve fluidly communicating with the fluid movement controller via a transfer line is interposed between the fluid movement controller and sampling needle. A second valve fluidly communicates with the sampling needle. A filter line is interposed between the first and second valves and communicates with a filter medium. A bypass line is interposed between the first and second valves. The first and second valves are adjustable alternately to define a first fluid conduit between the transfer line and the sampling needle through the filter line and to define a second fluid conduit between the transfer line and the sampling needle through the bypass line.

The workstation of the second embodiment of the present invention may include a second rack holder and a second automated arm assembly. The second automated arm assembly is adapted to effect programmable manipulations on the racks, including installing the racks in and removing the racks from the first and second rack holders and transporting the racks to and from the first and second rack holders. The first and second rack holders may be separate units or may be disposed adjacent to each other as a singular unit. Different types of racks, containing various types of vials or wells, may be loaded into the rack holders to permit a variety of crystallization and analysis methods to be performed on drug samples provided at the workstation.

The present invention also provides a process for preparing crystalline forms of drugs for crystal form screening. A filter assembly is provided which includes first and second valves, a filter line with a filter medium, and a bypass line. Each valve of the filter assembly has first, second and third ports. The filter line extends between the second port of the first valve and the second port of the second valve, and the bypass line extends between the third port of the first valve and the third port of the second valve. A mass of drug contained in a plurality of first vessels is then provided. A volume of solvent is added to the first vessels to dissolve a portion of the drug mass and to produce an unfiltered solution. The first vessels are agitated to enhance dissolution of the drug mass. The first and second valves are set to a filter mode by adjusting the first and second valves to define a fluid path from the first port of the second valve, through the filter line, and to the first port of the first valve. Predetermined quantities of the unfiltered solution are then withdrawn from the first vessels and caused to flow through the first port of the second valve, the filter line and the filter medium to produce a filtrate solution substantially free of solid-phase drug mass. The filtrate solution is caused to flow from the filter medium through the first port of the first valve and into a fluid holding container communicating with the first port of the first valve. The first and second valves are then set to a bypass mode by adjusting the first and second valves to define a fluid path from the first port of the first valve, through the bypass line, and to the first port of the second valve. The filtrate solution is caused to flow from the fluid holding container, through the bypass line, and to the first port of the second valve. Finally, predetermined quantities of the filtrate solution are dispensed from the first port of the second valve into a plurality of second vessels.

It is therefore an object of the present invention to provide an apparatus which permits automation of several of the procedural steps associated with the preparation, crystallization, crystal-form screening and solubility screening of drug samples, and a method for using such apparatus.

It is also an object of the present invention to provide a filtration assembly which may be used for liquid handling tasks as well as filtering tasks.

It is another object of the present invention to provide an apparatus which accomplishes preparation, transportation, crystallization, crystal-form screening, and solubility screening of drug samples using a single sampling instrument.

Some of the objects of the invention having been stated hereinabove, other objects will become evident as the description proceeds, when taken in connection with the accompanying drawings as best described hereinbelow.

BEST MODE FOR CARRYING OUT THE INVENTION

The first embodiment of the present invention is a modification of an existing liquid handling device. In order to afford a better appreciation of the invention, the existing device will first be described in its conventional form and normal application, and subsequently described in its modified, inventive form as adapted for automated crystal form screening and solubility determinations.

Figure 1:
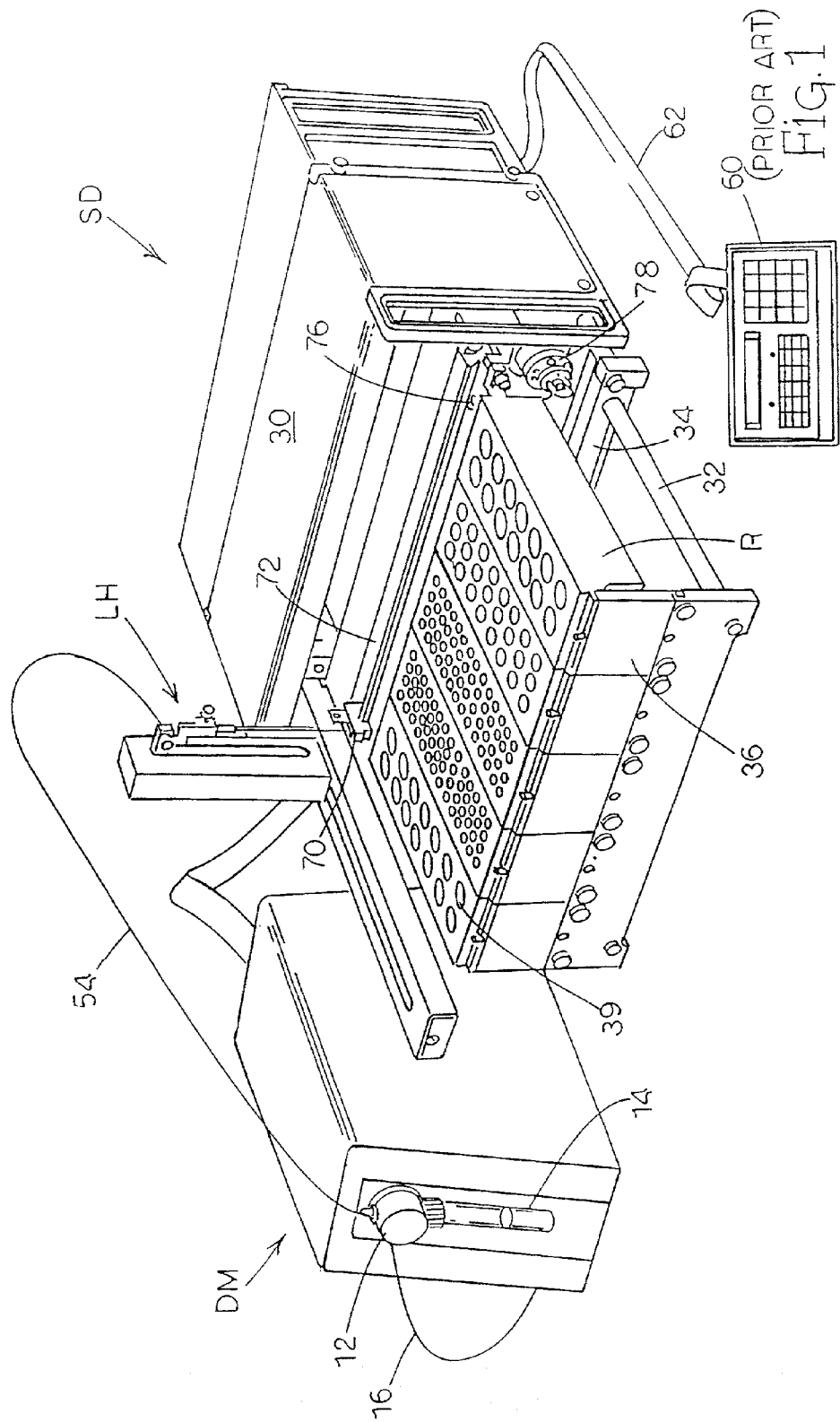
FIG. 1 is a perspective view of a liquid handling device of the prior art.
Figure 2:
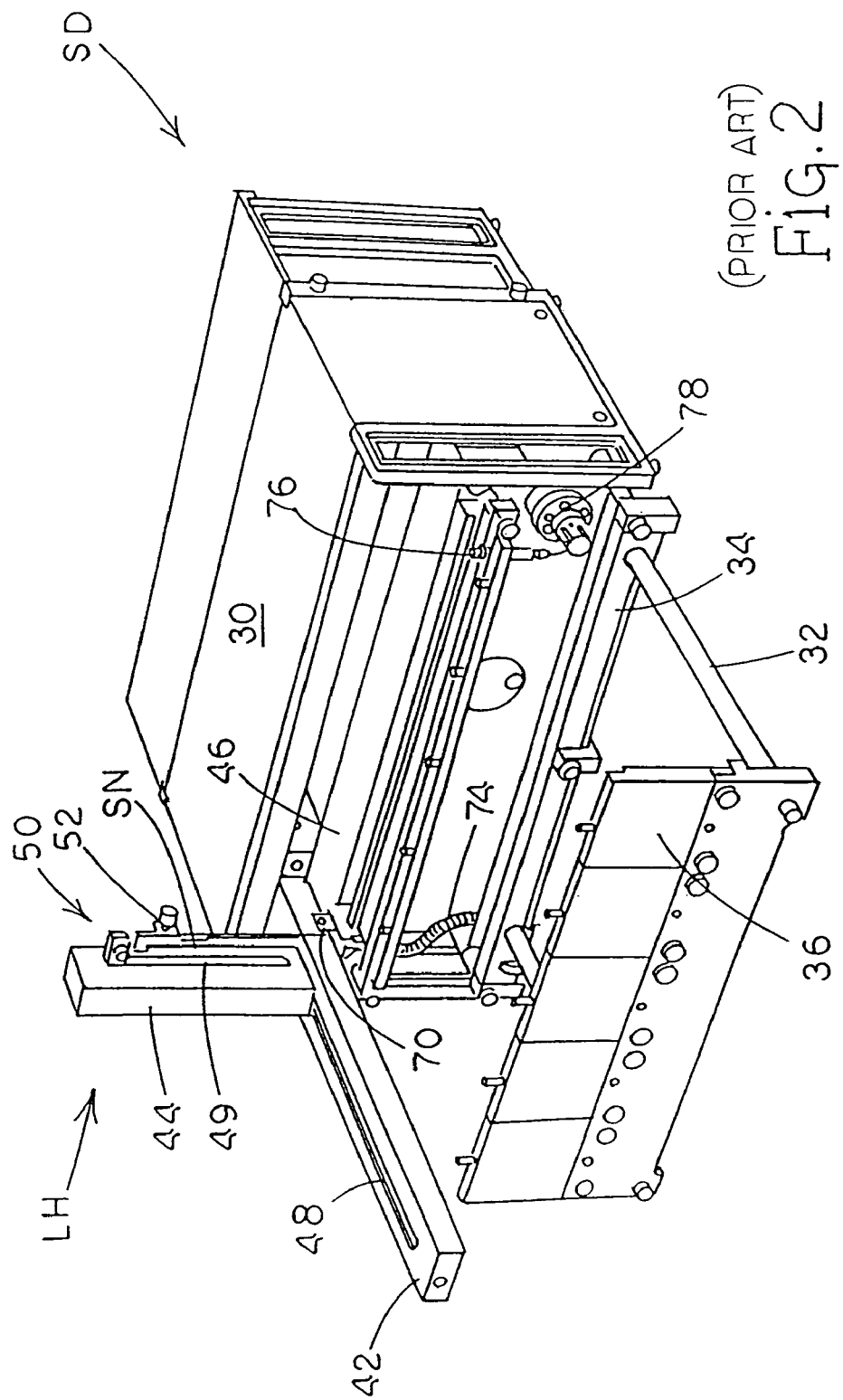
FIG. 2 is another perspective view of the prior art a liquid handling device of FIG. 1.

FIGS. 1 and 2 illustrate a particularly suitable liquid handling or sampling device generally designated SD from which the first embodiment of the present invention has been developed. Sampling device SD is available from Gilson Medical Electronics, Inc., and is known as the GILSON 232A Automatic Sample Processor and Injector (or GILSON Autosampler). Sampling device SD is generally used for sample preparation, and is capable of being programmed by means of written software to perform a wide variety of liquid handling and preparation tasks. For example, sampling device SD is equipped with an electrical input/output interface (not shown) to enable communication with a suitable liquid chromatography apparatus if desired.

As originally intended by the manufacturers of sampling device SD, a dilution module generally designated DM is provided, designated as the Dilutor 401, and is used to control the movement of liquid within various points of sampling device SD. A valve 12 is mounted to dilution module DM, and a syringe 14 depends therefrom. As is well known in the art, a movable boundary is disposed within syringe 14 and actuated by a stepper motor and associated drive unit (not shown) to provide both aspiration and positive pressure to fluid conduits of sampling device SD. The actuation may be programmed into sampling device SD. A length of solvent inlet tubing 16, preferably formed of PTFE, is connected to valve 12 to supply rinse solvent to sampling device SD.

Sampling device SD includes a main frame 30. A rack holder 32 is attached to main frame 30 and extends between a rack holding bar 34 and a series of rack adapter plates 36. As shown in FIG. 1, a plurality of racks R may be mounted on rack holder 32 through alignment with rack holding bar 34 and rack adapter plates 36. A wide variety of racks R, typically formed of either aluminum or polypropylene, are available depending on the desired application. Each rack R includes an array of wells or holes 39 for holding vials, test tubes or other vessels of differing sizes, to contain reagents, samples of liquid substances and the like.

Also attached to main frame 30 is a liquid handling subassembly generally designated LH. Liquid handling subassembly LH includes a horizontal arm 42, and a vertical arm 44. Horizontal arm 42 is slidably carried on a track 46 mounted within main frame 30. An additional track 48 is formed on horizontal arm 42, on which vertical arm 44 is slidably carried. A needle subassembly generally designated 50 is movably mounted to a vertically disposed track 49 of vertical arm 44. Needle subassembly 50 includes a sampling needle SN linked to vertical arm 44 via a needle holder 52. Sampling needle SN is used to load and extract liquid substances to and from different positions over and proximate to racks R. A length of transfer tubing 54, preferably formed of PTFE, provides fluid communication between sampling needle SN and valve 12 of dilution module DM. A stepper motor and associated drive (not shown) disposed within main frame 30 provide actuation for liquid handling subassembly LH. As in the case of dilution module DM, this actuation may be controlled by software interfacing with sampling device SD.

Thus, through the movement of horizontal arm 42, vertical arm 44 and needle subassembly 50, sampling needle SN may be programmed to accomplish a variety of liquid handling and sample preparation tasks, such as transferring solvent to vials disposed in racks R and transferring liquid substances from one vial to another vial. A remote keypad or computer 60 may be connected to sampling device SD via a ribbon cable 62 and used for entering instructions into memory, recalling previously written programs, and otherwise controlling the operation of the sampling device SD.

Sampling device SD also includes a rinsing station 70 which may be used for eliminating waste products and purging the fluid paths of sampling device SD between the operative steps of an intended procedure. Rinsing station 70 includes a polypropylene front trough 72 mounted to main frame 30. Front trough 72 extends parallel to racks R and is accessible by sampling needle SN. A drainage tube 74 depends from front trough 72. Also accessible by sampling needle SN is a fill port 76 leading to an injection valve 78. Fill port 76 and injection valve 78 are used to deliver samples to a liquid chromatography (HPLC) apparatus if desired.

As will be appreciated by those skilled in the art, the sampling device SD described hereinabove is quite useful for a number of liquid handling and preparation procedures, but is ill-suited and not intended for effecting many of the procedural steps required in the preparation and screening of crystal forms of drugs having potential pharmaceutical value. Accordingly, applicants have significantly modified sampling device SD in order to automate many of these procedural steps, taking advantage of the programmability of the various components of sampling device SD. The modification unexpectedly and surprisingly results in an efficient crystal form screening workstation CW, the structure and operation of which will now be described with particular reference to FIGS. 3–9.

Crystal form screening workstation CW is realized by integrating a novel dual-valve filtration assembly generally designated FA which is integrated into sampling device SD between dilution module DM and sampling needle SN. Filtration assembly FA includes first and second valves V1,V2, respectively. Preferably, each valve V1,V2 is a three-way valve having respective first, second and third ports 81–83 and 84–86. Transfer tubing 54 from dilution module DM is connected to first port 81 of first valve V1. A filter line FL is provided using a length of filter tubing 88 connected between second port 82 of first valve V1 and second port 85 of second valve V2. Likewise, a bypass line BL is provided using a length of bypass tubing 89 connected between third port 83 of first valve V1 and third port 86 of second valve V2. PTFE tubing having a 0.125 inch outside diameter and a 0.06 or 0.03 inch inside diameter has been found suitable for utilization in filter and bypass lines FL,BL, with lengths chosen according to desired internal volumes. A filter medium F may be installed anywhere along filter line FL in communication with filter tubing 88, but preferably is integrated into second port 82 of first valve V1. Preferable filter material is available from WHATMAN and classed as No. 1 qualitative paper. The filter material must be cut and sized to fit within second port 82.

Valves V1,V2 are available from General Valve Corporation as Model No. 1-17-900, and are rated at 20 psig. In the present embodiment, each valve V1,V2 has an internal passage 91,92 respectively, the orientation of which is switchable between a filter mode and a bypass mode depending on whether liquid is to flow through filter tubing 88 or bypass tubing 89. Actuation of valves V1,V2 is accomplished by means of a valve driver (not shown) that is preferably mounted within main frame 30. To provide communication between dilution module DM and sampling needle SN, transfer tubing 54 running from dilution module DM is connected to first port 81 of first valve V1, and a length of extension tubing 93 is connected between first port 84 of second valve V2 and sampling needle SN. Suitable valve fitting kits are available from UPCHURCH as Part Nos. P-307 and P-307S.

Figure 3:
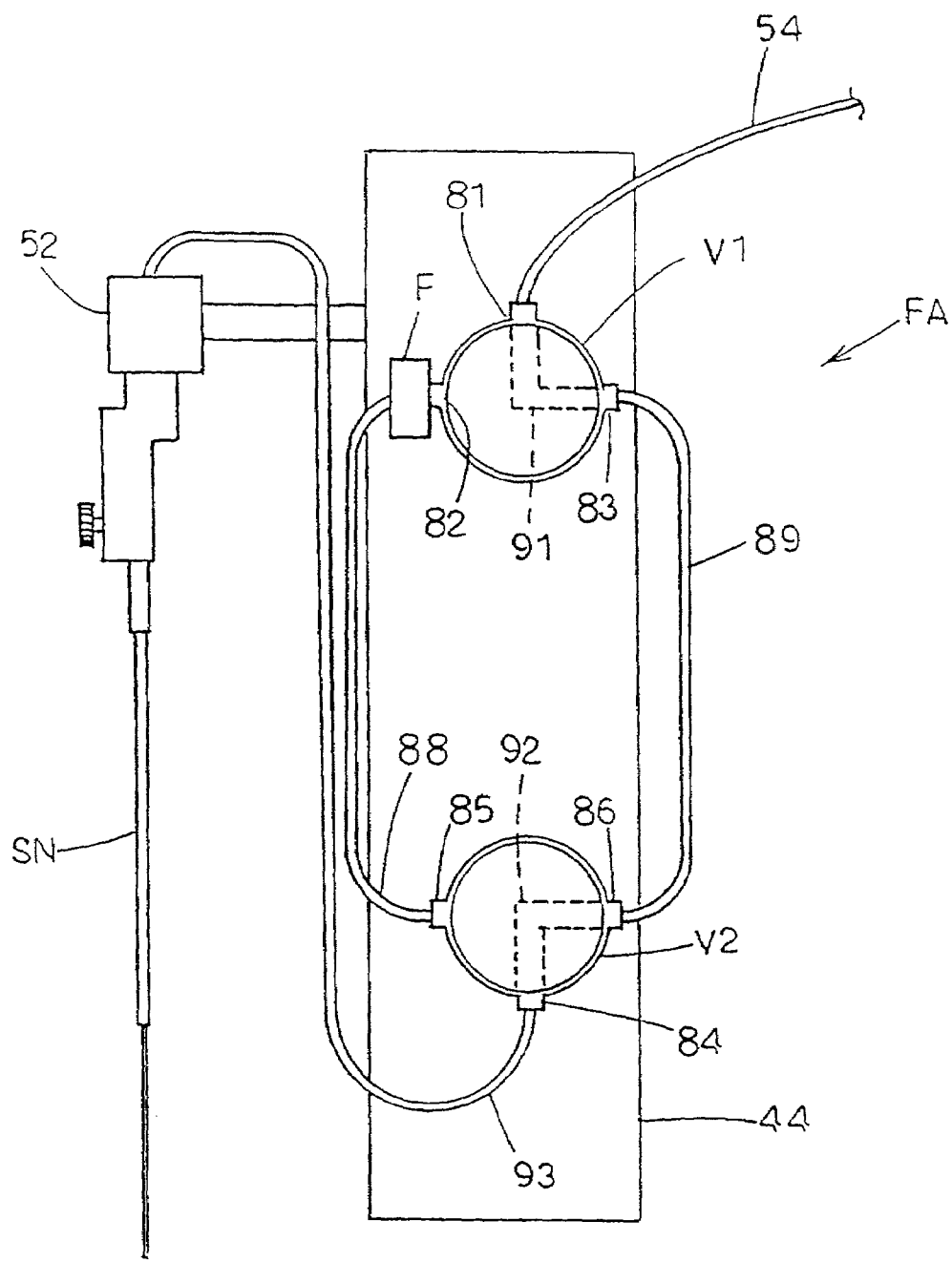
FIG. 3 is a side elevation view of a filtration assembly according to the present invention.
Figure 4:
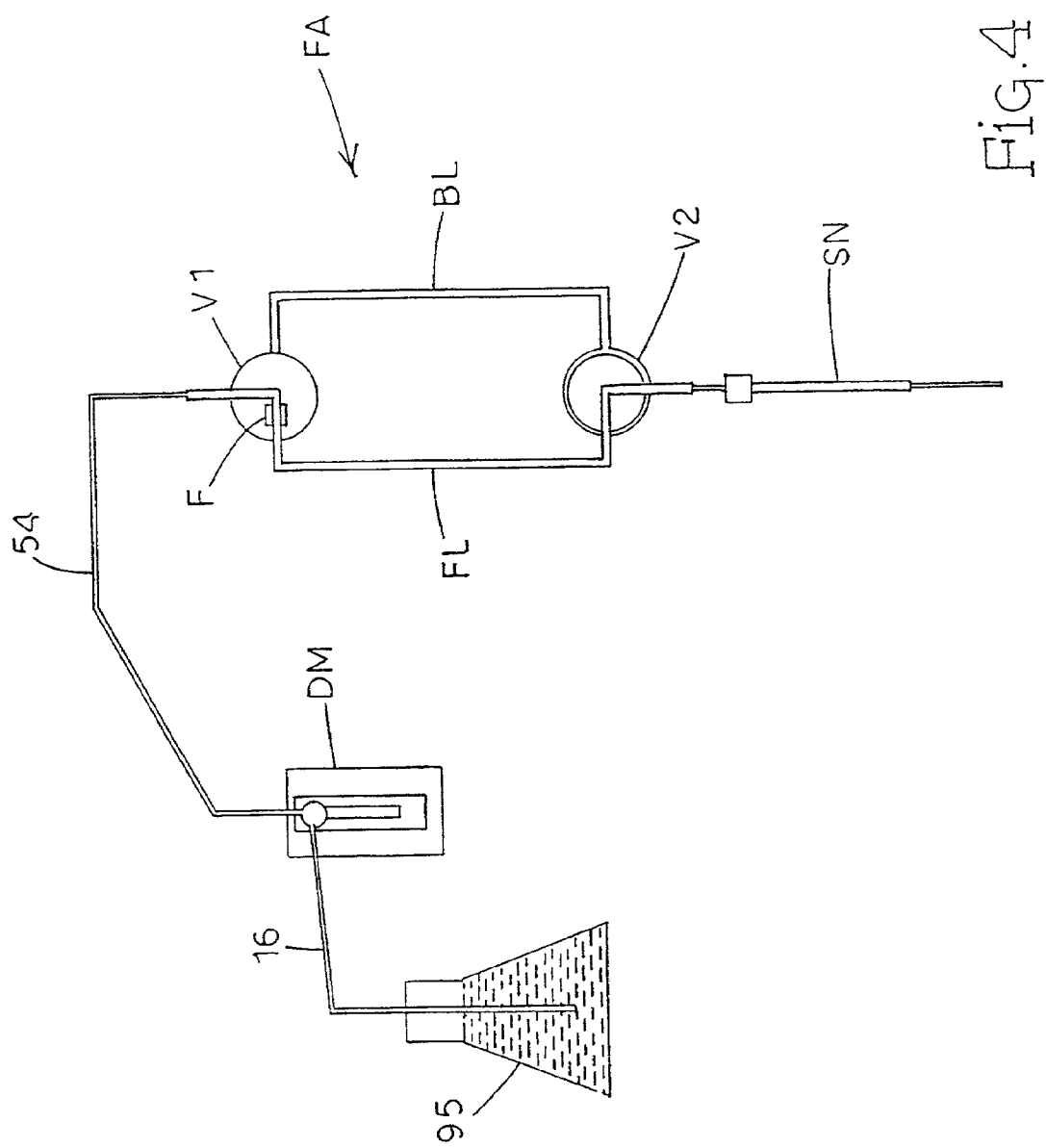
FIG. 4 is a diagrammatic view of the filtration assembly of FIG. 3.
Figure 5:
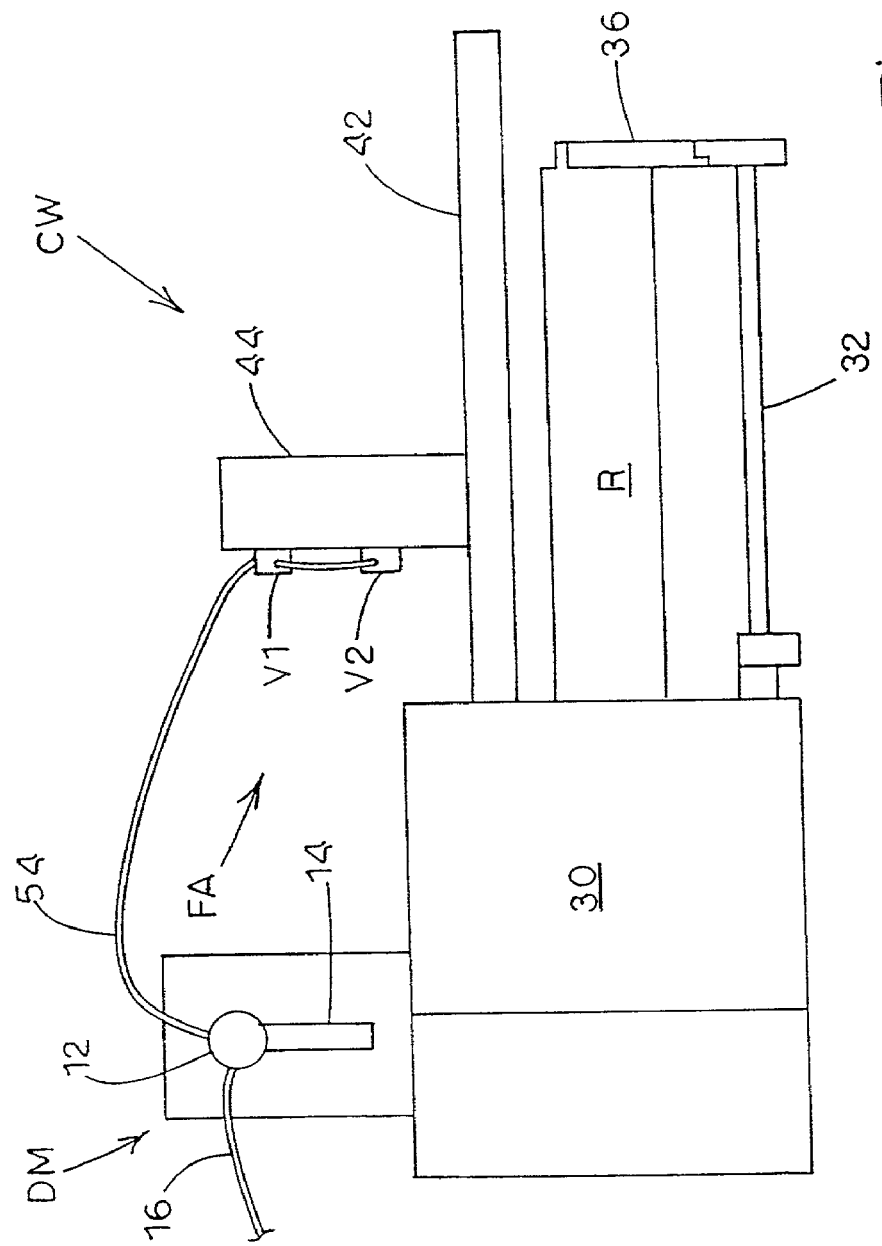
FIG. 5 is side elevation view of a crystal form screening workstation according to one embodiment of the present invention.
Figure 6:
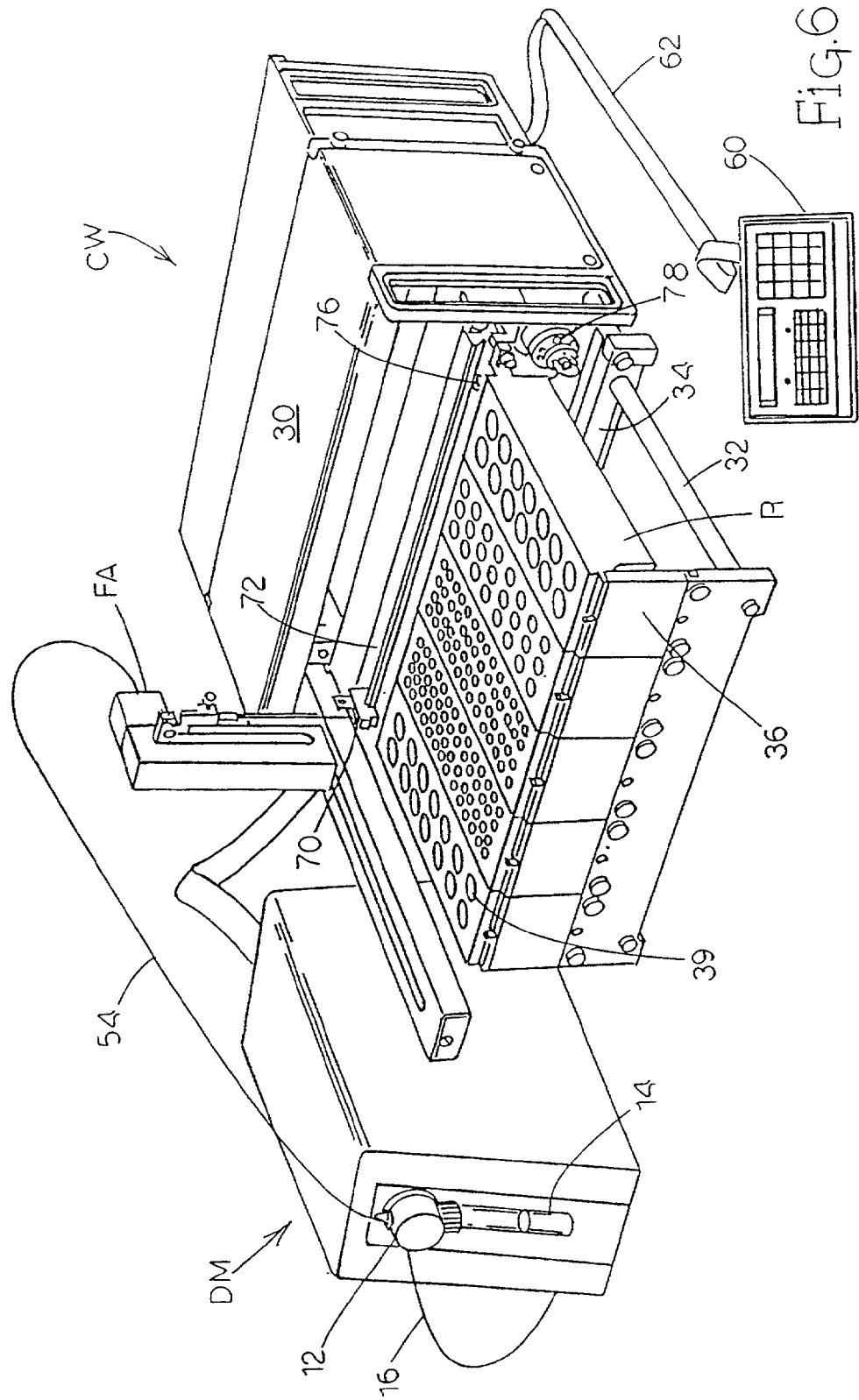
FIG. 6 is a perspective view of the workstation of FIG. 5.

While filtration assembly FA may be placed anywhere between dilution module DM and sampling needle SN, it has been found preferable to mount valves V1,V2 to vertical arm 44 of liquid handling subassembly LH as best shown in FIGS. 3, 5 and 6. This location is compatible with the pre-existing structure of workstation CW, and reduces the amount of extension tubing 93 needed.

Figure 7:
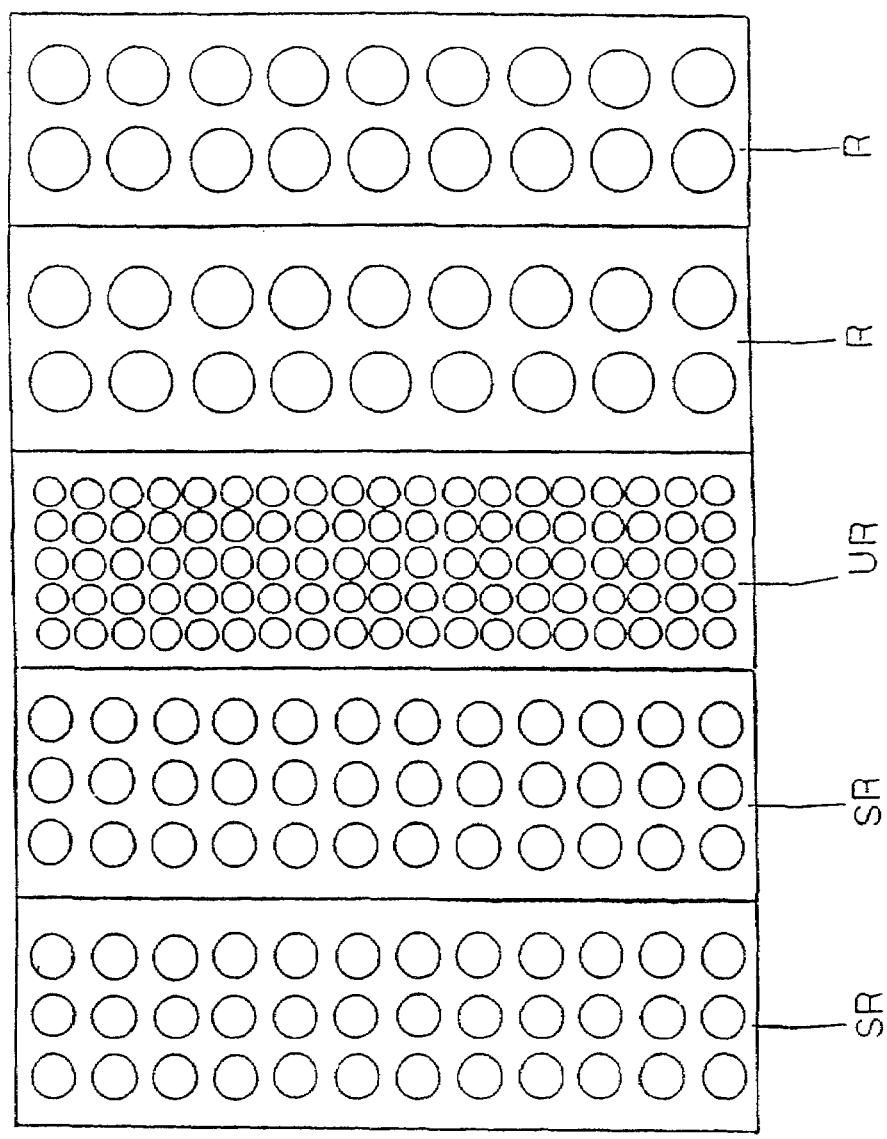
FIG. 7 is a top plan view of a configuration of racks according to the present invention.

The preferred operation of crystal form screening workstation CW will now be described. Workstation CW is favorably provided with a 1.0 mL syringe 14, 0.8 mm ID PTFE transfer tubing 54 with a 1.1 mL volume, a 250 mL needle rinse reservoir 95, and a sampling needle SN having a 123 mm height and a 0.42 mm ID beveled stainless steel septum piercing needle with a 0.8 mm ID sleeve. Racks R are initially set up as shown in FIG. 7. Two solvent racks SR are mounted in the leftmost positions of rack holder 32. The solvent racks SR are "Code 34" racks available from GILSON. Another of the racks UR has been modified to hold an ultrasonic bath. The particular ultrasonic bath chosen should be powerful enough to eliminate the need for manual vortexing commonly performed in experimental procedures. Suitable ultrasonic baths are available from GILSON and BRANSON. The remaining rack positions may initially be empty or contain one or more of the additional types of racks needed at subsequent stages of the screening process. These additional racks are described below. It should be noted that the particular GILSON model sampling device SD employed in connection with the present embodiment is limited to five standard-sized racks R. It should also be noted that racks R and the vials may be commercially available units, or may be customized according to user-defined specifications.

Solvent rack SR is provided with a plurality of solvent vials. Suitable solvent vials are available from KIMBLE as Part No. 60810W-1545, and are sized at 15×45 mm, 4 mL. Closures for the vials are also available from KIMBLE as Part No. 73804B-13425, and include a phenolic resin screw cap with a PTFE-faced, silicone-lined septum. The solvent vials are filled to appropriate volumes with a number of different solvents. Many types of solvents are available for experimental use in conjunction with crystal form screening. Examples include methanol, ethanol, water, acetonitrile, acetone, isopropanol, hexane, diethyl ether, and toluene. For each individual solvent vial, the type of solvent contained therein is identified by label and/or number and position data such as coordinates for the solvent vial are recorded.

Needle rinse reservoir 95 is placed in communication with solvent inlet tubing 16 and filled to an appropriate volume with a suitable rinse solvent such as water or acetonitrile. The ultrasonic bath apparatus is installed into ultrasonic rack UR and filled with water. A plurality of microvials are filled with an appropriate mass of a sample drug substance (e.g., approximately 1.0–100 mg, and typically 20 mg), and the mass is recorded. Each drug sample vial is identified by number and labeled appropriately. Suitable drug sample vials are manufactured by CHROMACOL and available from HEWLETT-PACKARD as Part No. HP 5180-0805, and are sized at 700 $\mu$L with an 8 mm neck. Closures for the vials are also available from WHEATON as Part No. 224234-07, and include an aluminum crimp top with a butyl polymer septum. After sealing, each drug sample vial is placed into one of the racks R. Preferably, the drug sample vials are placed into ultrasonic rack UR in order to eliminate the unnecessary step of transferring the drug sample vials to the ultrasonic bath from an additional rack. Dilution module DM is then actuated to draw a sufficient volume of rinse solvent from needle rinse reservoir 95 to flush all fluid lines.

After values representing the variables of (1) the number and coordinates of the samples and (2) the desired solvent volume for each sample are inputted into workstation CW, the dilution program is initiated. The program sets valves V1,V2 of filtration assembly FA to bypass mode, and cycles syringe 14 of dilution module DM to alternate between application of suction and positive pressure in the fluid lines. The program also actuates horizontal arm 42, vertical arm 44, and sampling needle SN as appropriate to move to and from the vials of solvent rack SR and the drug sample-containing vials of ultrasonic rack UR. In this manner, sampling needle SN is lowered into one of the solvent vials, and a predetermined amount of solvent (e.g., approximately 200–700 $\mu$L, but preferably 400 $\mu$L) is withdrawn therefrom, routed through bypass tubing 89, and held in transfer tubing 54. Sampling needle SN is then raised and moved to the target drug sample vial and inserted through the septum thereof. Flow in transfer tubing 54 is reversed, and the solvent injected into the drug sample vial. This process is repeated a predetermined number of times to introduce solvent into each drug sample vial. Additionally, workstation CW may programmed to mix two or more different types of solvents in a given drug sample vial to create binary, tertiary, quaternary, etc. solvent systems.

Figure 8:
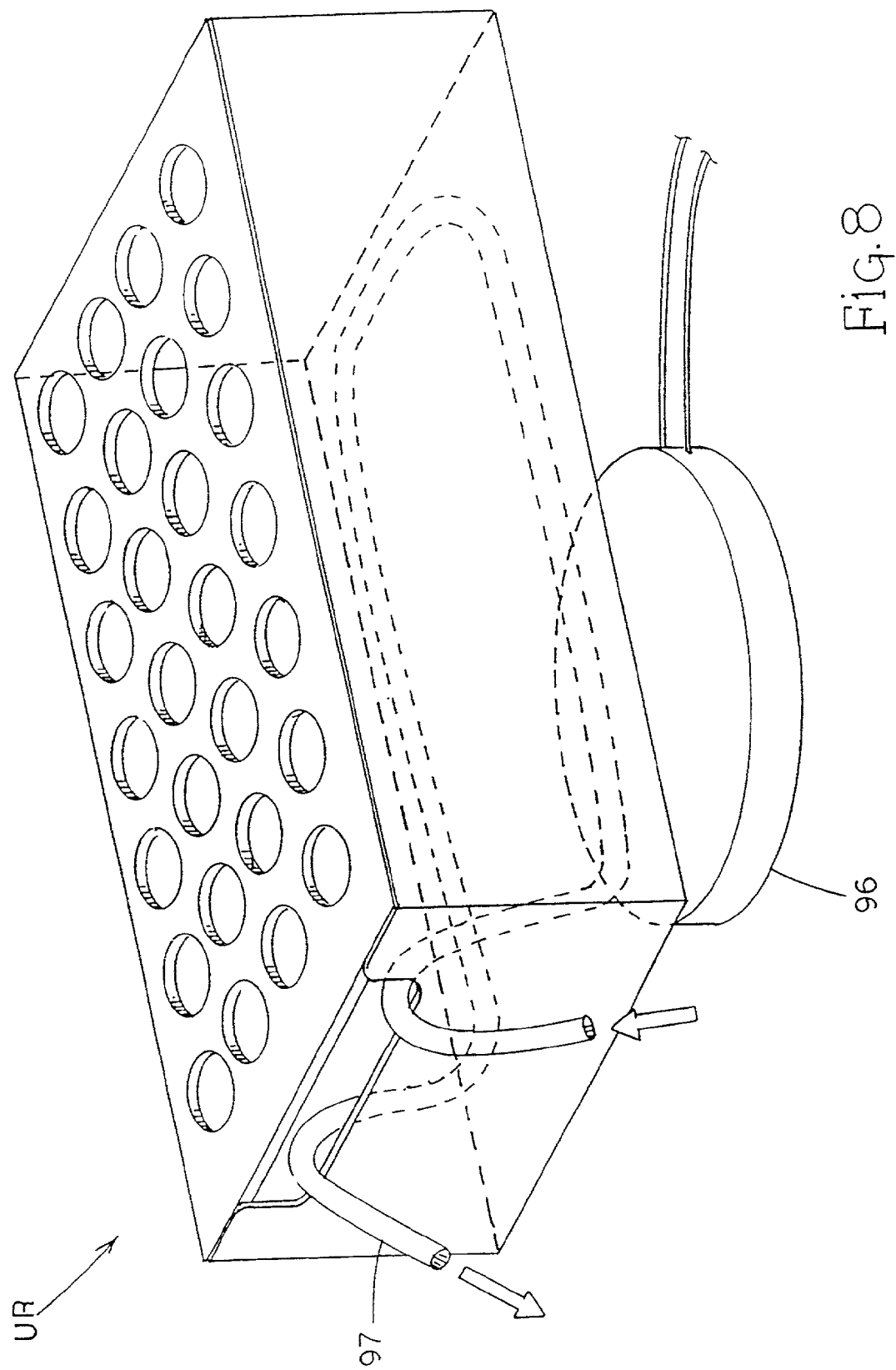
FIG. 8 is a perspective view of an ultrasonic rack used in accordance with the present invention.

The program then initiates the sonication process, which agitates the drug sample vials and ensures that particles of the solid-phase drug mass are sufficiently wetted. Because heat energy may adversely influence the solubility characteristics of the drug, the ultrasonic bath typically is cycled on and off at given intervals (e.g., 10 min. sonication period every 30 min.) in order to minimize sample heating. Hence, a sonication period of up to twenty-four hours is typically required to achieve proper dissolution of the drug samples. However, the sonication period may be significantly reduced by providing an active cooling system for the ultrasonic bath. A metal conduit with sufficient heat transfer characteristics has been found suitable for this purpose. Thus, ultrasonic rack UR with ultrasonic drive 96 may be adapted to receive a length of copper tubing 97 placed in contact with the ultrasonic bath, as shown in FIG. 8. Copper tubing 97 is connected to heat transfer equipment (not shown) of known design, and water or other suitable fluid medium is circulated through copper tubing 97 to carry heat towards or away from the ultrasonic bath. The addition of copper tubing 97 permits the sonication process to proceed on a constant, substantially isothermal basis.

Figure 9:
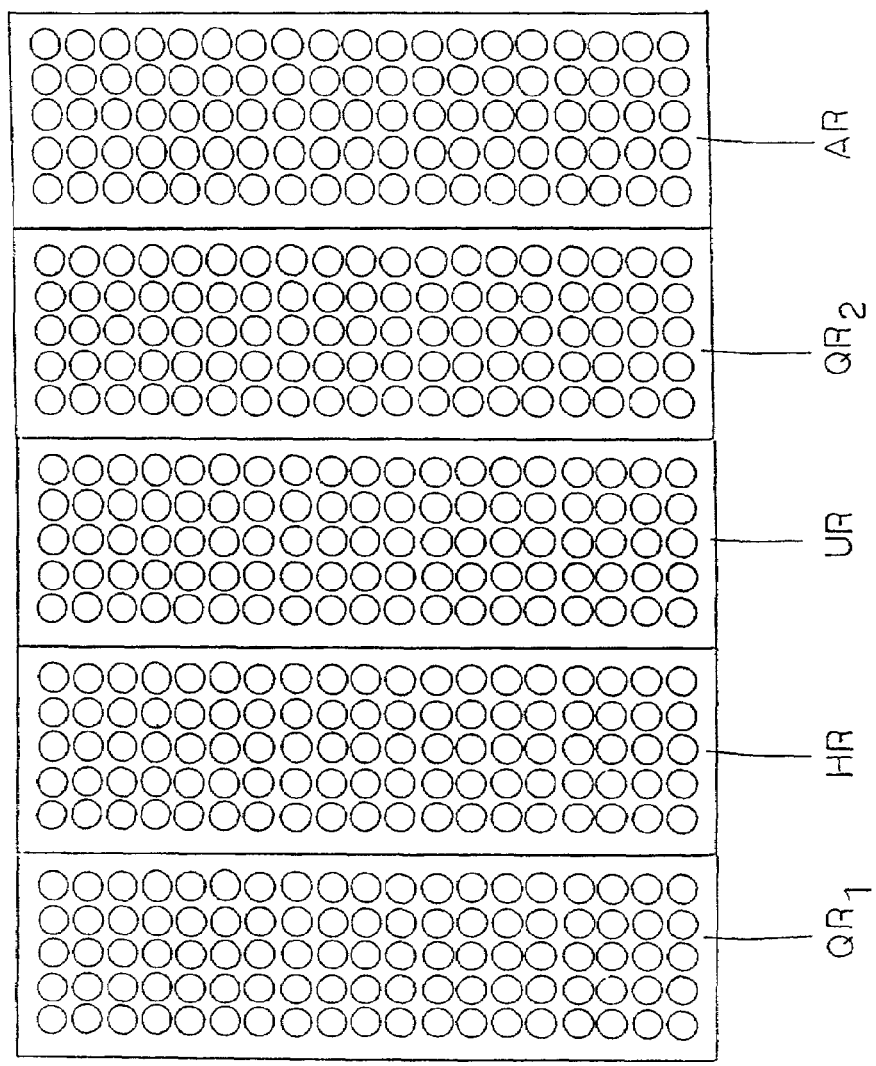
FIG. 9 is a top plan view of a second configuration of racks according to the present invention.

After sonication, the drug samples are ready for crystallization, and visual observations regarding each drug sample vial may be made and recorded. Because additional, different types of racks will be needed for the crystallization and analysis stages, rack holder 32 must be reconfigured. FIG. 9 illustrates one possible configuration.

It is expected that most of the drug sample vials will contain a suspension—that is, in addition to the resulting saturated solutions, the vials may contain residual quantities of undissolved, solid-phase drug. If desired, a quartz microtitre plate (preferably having an array of 96 wells) may be installed into one of the racks R of workstation CW, e.g., rack $QR_1$ in FIG. 9. A suitable quartz plate is available from Hellma Cells Inc. as Part No. 730.009-Q. An aliquot (e.g., typically 25 $\mu$L) of the suspension may be extracted from each drug sample vial of ultrasonic rack UR and dispensed into wells of the quartz plate of rack $QR_1$, the translucent quality of the quartz enabling examination of the optical and spectral properties of the material in each well. Workstation CW may be programmed for this purpose, by setting filtration assembly FA to bypass mode and employing sampling needle SN to meter the appropriate amount of suspension into the wells of the quartz plate.

In order to complete the preparation of the drug samples for proper crystallization, the solution containing the dissolved drug must be separated from the residual solid-phase drug mass. Workstation CW is programmed to utilize filtration assembly FA for this purpose. Also, a holding rack HR is mounted in rack holder 32 containing an array of holding vessels or vials corresponding to the array of drug sample vials residing in the ultrasonic rack UR. Suitable holding vials are available from Alltech as Part No. 98148, dimensioned at 700 $\mu$L with an 8-mm neck, and provided with the previously described WHEATON closure.

The fluid conduits of workstation CW, including sampling needle SN, are flushed using a solvent such as acetonitrile supplied from needle rinse reservoir 95. If necessary, valves V1,V2 of filtration assembly FA may be alternately set to filter and bypass modes to flush both filter and bypass tubing 88,89. Prior to filtration, however, workstation CW is programmed to ensure the filter mode is enabled. Then, for each drug sample vial, sampling needle SN is employed to extract the remaining volume of suspension (e.g., approximately 300 $\mu$L). Again, this procedure is automated by programming workstation CW appropriately, with user-inputted values representing the variables of (1) the number of samples and (2) the sample volume. The suspension is pulled through filter tubing 88 and across filter medium F, thereby producing a filtrate solution. With syringe 14 still aspirating the system, the filtrate solution is pulled through first valve V1 and into transfer tubing 54 while the solid-phase drug particles are held in filter tubing 88. Sampling needle SN travels along a predetermined path to a designated target holding vessel of holding rack HR. Valves V1,V2 are switched to close filter line FL and open bypass line BL. Sampling needle SN is then inserted into the holding vessel and the filtrate solution held in transfer tubing 54 is dispensed therein. This process is repeated for each drug sample vial. As a result, the array of holding vessels in holding rack HR contain a plurality of filtrate solutions representing varied amounts of drug dissolved in varied solvent systems.

The apparatus and method of the present invention also permits solutions to be filtered by "pushing" the solution through the filter medium F rather than "pulling" the solutions through, which in many cases allow the filtration to progress more rapidly. Accordingly, filtration assembly FA may be programmed to set valves V1, V2 initially in the bypass mode. The unfiltered solution is extracted from one of the drug sample vials and routed directly into transfer tubing 54 via bypass line BL. Sampling needle SN travels to target holding vessel, and syringe 14 of dilution module DM applies positive pressure to the fluid system. Valves V1, V2 are set to filter mode. The unfiltered solution is sent through filter medium F, and the resulting filtrate solution is injected into the target holding vessel. At this point, a flushing step may be performed to purge filtration assembly FA of solid-phase material.

The filtrate solutions contained in the holding vessels are now prepared for any number of desired analyses and tests. Specified volumes (e.g., 25 $\mu$L) of filtrate solutions may at this point be transported via sampling needle SN to the vessels or vials of additional racks, with each rack configured for the appropriate analysis. Importantly, the present invention contemplates that crystallization procedures may be conducted in one or more of the additional racks. For instance, a 96 well quartz microtitre plate as described above may be installed in a rack $QR_2$ in which to conduct evaporative crystallization. The quartz construction provides a chemically resistant surface that is optically transparent and hence amenable to direct analysis in situ by optical microscopy to compare and differentiate the shapes, sizes and degrees of crystallinity of the various crystal forms produced. Raman spectroscopy may also be conducted using the quartz microtitre plate.

Evaporative crystallization may additionally or alternatively be conducted in a rack AR containing a 96 well polypropylene microtitre plate with aluminum pans inserted into the wells. The polypropylene plate is available from Corning Costar Corp., and the aluminum pans are available from TA Instruments as Part No. 900794.901. The evaporative crystallization products generated in the polypropylene plate may be analyzed using optical microscopy, Raman spectroscopy, and differential scanning calorimetry (DSC) methods. If more than one type of analysis is to performed on the crystallization products, workstation CW can be programmed to account for different sample volumes of filtrate and multiple racks. For example, the program may instruct the sampling needle to withdraw 100 $\mu$L of filtrate solution from holding vessel No. 1, travel to a quartz microtitre plate used for optical microscopy, and deposit the filtrate solution into well No. 1 of the quartz microtitre plate. In like manner, the program may instruct the sampling needle to travel to well No. 1 of an adjacent polypropylene microtitre plate used for DSC testing and deposit 100 $\mu$L of filtrate solution therein.

In addition or as an alternative to evaporative crystallization, cooling crystallization may be performed to produce crystal forms from the filtrate solutions contained in the holding vessels. A temperature-controlled rack may be substituted into the configuration of FIG. 9 for this purpose, to which filtrate solutions from the holding vessels may be transported via sampling needle SN. Preferably, a FISHER Model No. 9110 recirculating bath with a programmable cooling profile is employed to carry out the cooling crystallization.

Apart from the crystallization and analytical procedures just described, workstation CW may be programmed to withdraw aliquots (e.g., 25 $\mu$L) of the filtrate solution from the holding vessels and inject the samples into liquid chromatography apparatus in order to make equilibrium solubility determinations.

As will be readily apparent from the above description, the first embodiment of the present invention automates several of the steps involved in the crystal form screening process. However, because the first embodiment utilizes a pre-existing sampling device not specifically intended to meet the objects of the present invention, applicants have encountered some limitations in its use. Significantly, the five-rack configuration of the sampling device cannot simultaneously accommodate the use of every type of rack required in effecting every stage of the procedures described herein. Human interaction is required to change out racks R and reload rack holder 32. Applicants have therefore developed additional embodiments of the crystal form screening workstation CW to overcome the limitations of the first embodiment. Each workstation CW described hereafter is sui generis; that is, each crystal form screening workstation CW is designed specifically for the purpose of increasing the degree of automation of the preparation, crystallization, and analysis steps. Yet, as will become apparent, the new workstations CW retain the advantageous utilities of the first embodiment described hereinabove.

Figure 10:
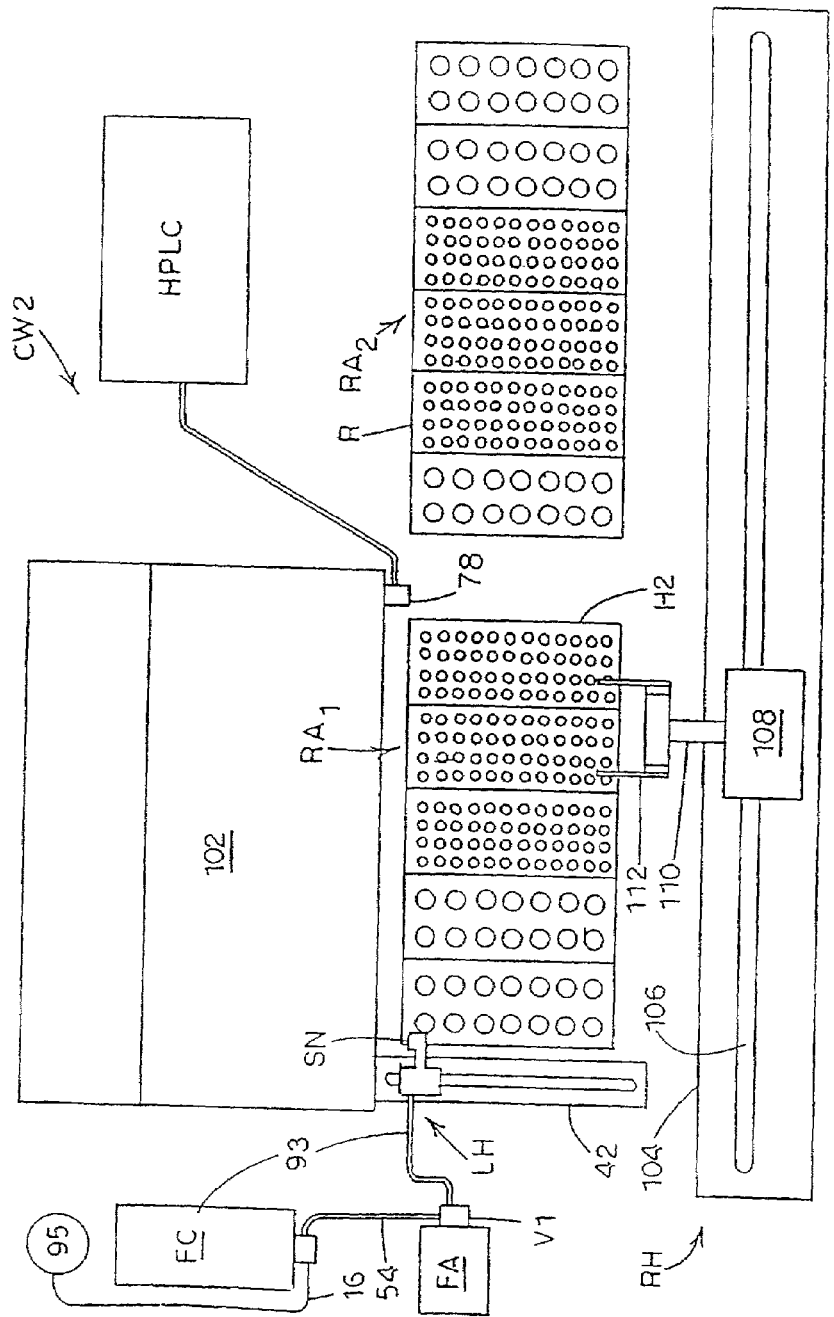
FIG. 10 is a top view of a crystal form screening workstation according to a second embodiment of the present invention.

Accordingly, FIG. 10 illustrates a second embodiment of the present invention. A workstation generally designated CW2 includes a mainframe 102 which houses memory, logic control, and all other necessary components for interface with a computer (not shown). A fluid flow controller FC controls all fluid flow throughout workstation CW2. Flow controller FC may be any device or combination of devices capable of applying both positive and negative pressure to the fluid conduits of the workstation and of accurately metering fluid through transfer tubing 54 and sampling needle SN. For example, an air pump or peristaltic pump in combination with a solenoid-actuated manifold and vacuum generator could be used. It is preferable, however, to retain the syringe 14 employed in conjunction with the dilution module DM described above. It is also preferable to provide a liquid handling subassembly LH similar to that described earlier to manipulate sampling needle SN. All motors and drive needed to actuate flow controller FC and liquid handling subassembly LH are preferably mounted within main frame 102. Filtration assembly FA includes applicants' novel dual-valve design as described above. Filtration assembly FA may be mounted to liquid handling subassembly LH as before, or it may be provided as a separate module as shown in FIG. 10.

In order to accommodate all types of racks used in the preparation, crystallization and analytical procedures described above, two rack assemblies $RA_1$, $RA_2$ are provided. A rack handling subassembly RH is provided to load, transport and remove the various racks R to and from rack assemblies $RA_1$, $RA_2$ in accordance with the desired protocol. Rack handling subassembly RH includes a horizontal member 104 having a track 106 in which a vertical member 108 rides. A telescoping boom 110 movably connected to vertical member 108 operates a boom head 112. Both boom head 112 and racks R are adapted to permit boom head 112 to releasably engage racks R. As in the case of liquid handling subassembly LH, movements of rack handling subassembly RH are controlled through interface with software provided with workstation CW2. The instrumentation (not shown) used to screen the crystal forms produced may be placed on or in main frame 102 or set up in the vicinity of rack assembly $RA_2$. For example, in FIG. 10 liquid chromatography apparatus HPLC has been disposed in operable communication with an injection valve 78 of main frame 102. Workstation CW2 is otherwise similar to workstation CW of the first embodiment.

Figure 11:
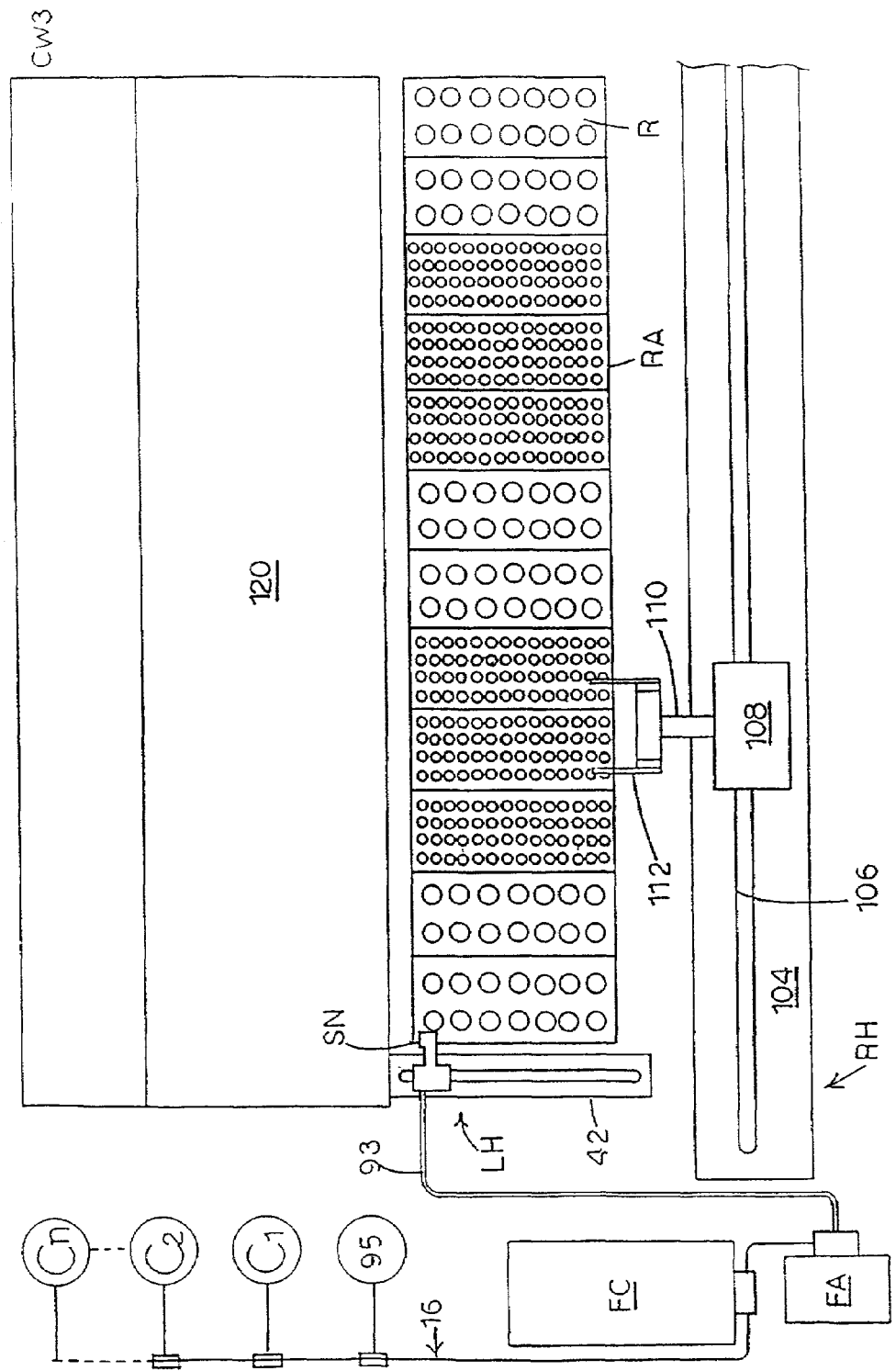
FIG. 11 is a top view of a crystal form screening workstation according to a third embodiment of the present invention.

FIG. 11 illustrates a third embodiment of the present invention. A workstation generally designated CW3 includes an extended-length main frame 120 adapted to house all instrumentation, motors, and logic components needed to perform the screening procedures described herein. A distinctive feature of workstation CW3 is a single rack assembly RA that holds every rack R required in the above-described procedures. Single rack assembly RA extends parallel to the entire length of main frame 120. As a result, every vial or well contained in every rack R of the workstation CW3 is accessible by sampling needle SN, thereby providing even greater flexibility and in situ operation. Nevertheless, an extended-length rack handling subassembly RH may be provided to transport racks off-site (e.g., to another workstation) if desired. Also shown in FIG. 11 are a plurality of liquid reservoirs or containers $C_1$–$C_n$ disposed in fluid communication with sampling needle SN, in addition to needle rinse reservoir 95. These containers $C_1$–$C_n$ may be used to temporarily store various liquids as needed (e.g., multiple types of solvents used for crystallization or dilution). Workstation CW3 is otherwise similar to workstations CW and CW2 described heretofore.

It will be understood that various details of the invention may be changed without departing from the scope of the invention. Furthermore, the foregoing description is for the purpose of illustration only, and not for the purpose of limitation—the invention being defined by the claims.

What is claimed is:

1. A crystal form screening workstation comprising:
   (1) a plurality of racks removably mounted to a first rack holder, each rack adapted to hold a plurality of vessels;
   (2) sampling means movably mounted to a first automated arm assembly, the first automated arm assembly adapted to effect programmable manipulations of the sampling means along paths extending within the vessels and over the racks;
   (3) a fluid movement controller adapted to withdraw fluid from and deliver fluid to the vessels of the racks through the sampling means;
   (4) a first valve fluidly communicating with the fluid movement controller via a transfer line interposed therebetween;
   (5) a second valve fluidly communicating with the sampling means;
   (6) a filter line interposed between the first and second valves;
   (7) a filter medium disposed in or at an end of the filter line; and
   (8) a bypass line interposed between the first and second valves, wherein the first and second valves are adjustable alternately to define a first fluid conduit between the transfer line and the sampling means through the filter line and to define a second fluid conduit between the transfer line and the sampling means through the bypass line.

2. The workstation according to claim 1 wherein the sampling means is a needle having a channel through which fluid can pass.

3. The workstation according to claim 1 wherein one of the racks holds an ultrasonic bath.

4. The workstation according to claim 3 wherein the ultrasonic bath includes means for transferring ultrasonic energy cyclically at predetermined intervals.

5. The workstation according to claim 4 wherein the ultrasonic transferring means includes a thermostat.

6. The workstation according to claim 3 wherein the ultrasonic bath includes a cooling tube disposed in contact with liquid residing in the bath, the cooling tube adapted to permit a heat transfer medium to be circulated therethrough to regulate the temperature of the bath.

7. The workstation according to claim 1 wherein one of the racks is a quartz microtitre plate.

8. The workstation according to claim 1 wherein one of the racks holds an array of wells.

9. The workstation according to claim 1 wherein one of the racks includes a bracket adapted to hold an array of vials.

10. The workstation according to claim 1 wherein the first automated arm assembly includes:
    (1) a vertical arm mechanically linked to the sampling means and adapted to permit vertical translation of the sampling means along a z-axis;
    (2) a horizontal arm slidably connected to a frame of the workstation and adapted for horizontal translation along an x-axis, wherein the vertical arm is movably mounted to the horizontal arm to permit horizontal translation of the vertical arm along a y-axis; and
    (3) a motor assembly in actuating engagement with the horizontal and vertical arms to control manipulation of the sampling means along programmable paths.

11. The workstation according to claim 1 further comprising a second automated arm assembly adapted to effect programmable manipulations on the racks including installing the racks in and removing the racks from the first rack holder.

12. The workstation according to claim 1 further comprising a second rack holder and a second automated arm assembly adapted to effect programmable manipulations on the racks including installing the racks in and removing the racks from the first and second rack holders and transporting the racks to and from the first and second rack holders.

13. The workstation according to claim 12 wherein the first and second rack holders are joined as a single unit.

14. The workstation according to claim 12 wherein the second automated arm assembly includes a base having a slot, a boom support member disposed in moving engagement with the slot, a boom extending from the boom support member, and a boom head disposed on an end of the boom and adapted to releasably engage the racks.

15. The workstation according to claim 1 wherein the fluid movement controller includes:
    (1) a syringe comprising a column and a movable boundary disposed within the column; and
    (2) a third valve fluidly communicating with a fluid supply source, the syringe, and the transfer line.

16. The workstation according to claim 15 wherein the movable boundary is actuated by a stepper motor.

17. The workstation according to claim 1 further comprising a fluid reservoir communicating with the fluid movement controller.

18. The workstation according to claim 1 further comprising an injector adapted to receive fluid from the sampling means and deliver fluid to a liquid chromatography device.

* * * * *